(12) United States Patent
Crichton

(10) Patent No.: US 10,974,271 B2
(45) Date of Patent: Apr. 13, 2021

(54) FLUID MANAGEMENT FOR VIBRATING PERFORATE MEMBRANE SPRAY SYSTEMS

(71) Applicant: The Technology Partnership Plc., Royston (GB)

(72) Inventor: Daniel Crichton, Cambridge (GB)

(73) Assignee: THE TECHNOLOGY PARTNERSHIP PLC, Royston (GB)

(*) Notice: Subject to any disclaimer, the term of this patent is extended or adjusted under 35 U.S.C. 154(b) by 101 days.

(21) Appl. No.: 15/021,436

(22) PCT Filed: Sep. 12, 2014

(86) PCT No.: PCT/GB2014/052758
§ 371 (c)(1),
(2) Date: Mar. 11, 2016

(87) PCT Pub. No.: WO2015/036764
PCT Pub. Date: Mar. 19, 2015

(65) Prior Publication Data
US 2016/0228902 A1    Aug. 11, 2016

(30) Foreign Application Priority Data
Sep. 13, 2013  (GB) ..................................... 1316314

(51) Int. Cl.
*B05B 17/00* (2006.01)
*B05B 11/00* (2006.01)
(Continued)

(52) U.S. Cl.
CPC ............ *B05B 17/0646* (2013.01); *A61L 9/00* (2013.01); *A61M 35/00* (2013.01);
(Continued)

(58) Field of Classification Search
CPC ............ B05B 17/0646; B05B 17/0676; B05B 17/0684; A01M 15/0085; A61M 15/0085
(Continued)

(56) References Cited

U.S. PATENT DOCUMENTS 3,159,176 A * 12/1964 Russell ................... B60T 11/28
137/493.1
4,533,082 A    8/1985 Maehara et al.
(Continued)

FOREIGN PATENT DOCUMENTS

EP    1205199 A1    5/2002
EP    2293882 A1    3/2011
(Continued)

OTHER PUBLICATIONS

International Search Report to corresponding International Appl. No. PCT/GB2014/052753, dated Feb. 18, 2015, 4 pages.

*Primary Examiner* — Alex M Valvis
(74) *Attorney, Agent, or Firm* — Tarolli, Sundheim, Covell & Tummino LLP

(57) ABSTRACT

A droplet generation device comprising a reservoir split into at least two regions by a substantially liquid impermeable barrier, a perforate membrane connecting one of said regions, containing, in use, the liquid to be dispensed, to the atmosphere, such that vibration of the membrane causes the liquid to be ejected through the perforate membrane into the atmosphere, and a pressure control system consisting of one or more valves in which at least one valve vents gas into the reservoir in response to a pressure difference, $\Delta P_{in}$, across it that is less than zero, and at least one valve is connected to a non-liquid-containing region of the reservoir and vents gas out of the reservoir in response to a pressure difference, $\Delta P_{out}$, across it that is greater than $\Delta P_{in}$, where $\Delta P_{in}$ and $\Delta P_{out}$ are the absolute pressure of the gas in the reservoir (Continued)

Figure 1:
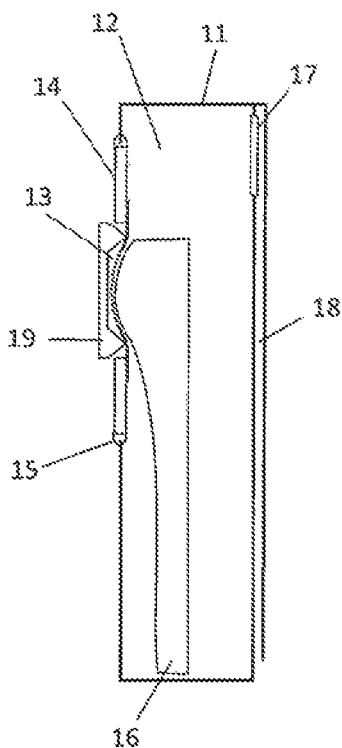
Figure 2:
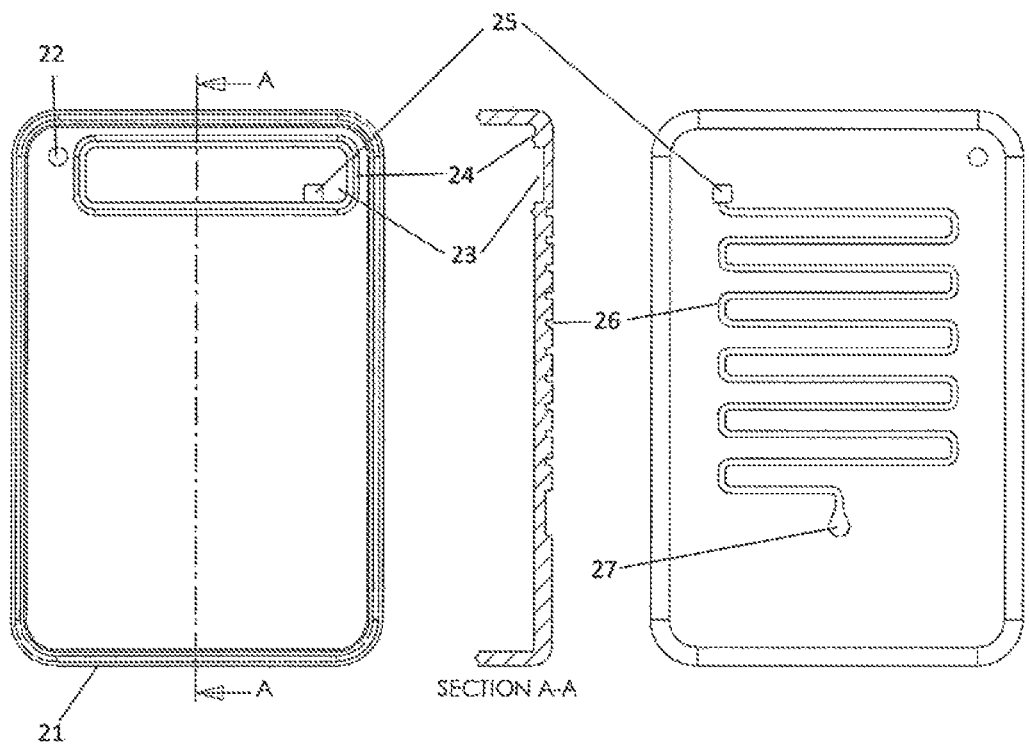
Figure 3:
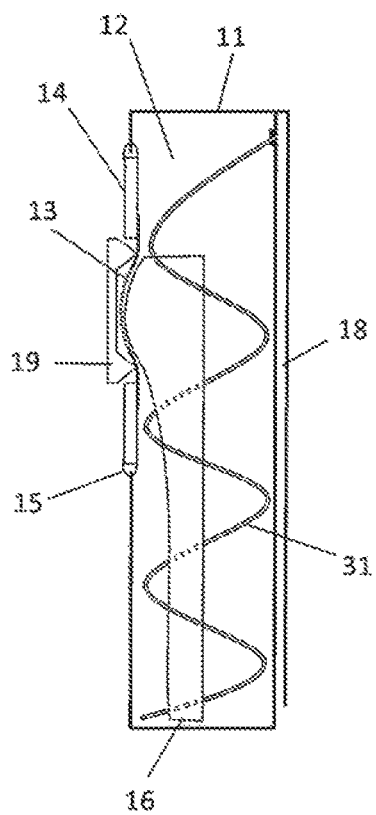

minus the absolute atmospheric pressure outside of the reservoir.

12 Claims, 4 Drawing Sheets

(51) Int. Cl.
    *A61L 9/00*     (2006.01)
    *B05B 17/06*     (2006.01)
    *A61M 35/00*     (2006.01)
    *A61M 11/00*     (2006.01)

(52) U.S. Cl.
    CPC ...... *B05B 11/0039* (2018.08); *B05B 11/0054* (2013.01); *B05B 11/00442* (2018.08); *B05B 17/0638* (2013.01); *B05B 17/0684* (2013.01); *A61M 11/005* (2013.01); *B05B 11/00412* (2018.08)

(58) Field of Classification Search
    USPC .................. 137/846–850, 493.1–493.6, 854
    See application file for complete search history.

(56) References Cited

U.S. PATENT DOCUMENTS

| | | |
|---|---|---|
| 5,487,378 A | 1/1996 | Robertson et al. |
| 5,518,179 A * | 5/1996 | Humberstone ..... B05B 17/0646 |
| | | 239/102.2 |
| 5,718,222 A * | 2/1998 | Lloyd ................ A61K 51/1206 |
| | | 128/200.14 |
| 5,823,428 A | 10/1998 | Humberstone et al. |
| 6,113,001 A | 9/2000 | Sant et al. |
| 6,446,878 B1 * | 9/2002 | Chandra ................... B05B 9/04 |
| | | 222/420 |
| 6,581,852 B2 | 6/2003 | Garcia et al. |
| 7,357,133 B2 * | 4/2008 | Goodchild ........ A61M 15/0065 |
| | | 128/200.14 |
| 7,694,892 B2 | 4/2010 | Feriani et al. |
| 9,611,452 B2 * | 4/2017 | Singh ........................ C12H 1/22 |
| 2006/0011737 A1 * | 1/2006 | Amenos .............. B05B 17/0684 |
| | | 239/102.1 |

FOREIGN PATENT DOCUMENTS

| | | |
|---|---|---|
| WO | 2009150619 A1 | 12/2009 |
| WO | 2012156724 A2 | 11/2012 |

* cited by examiner

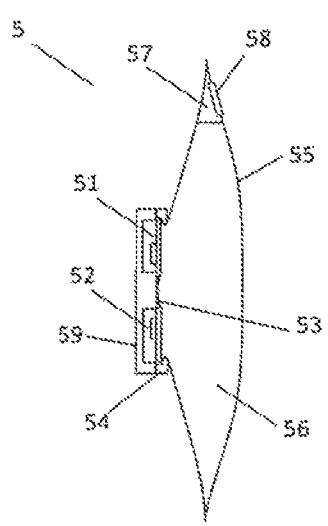
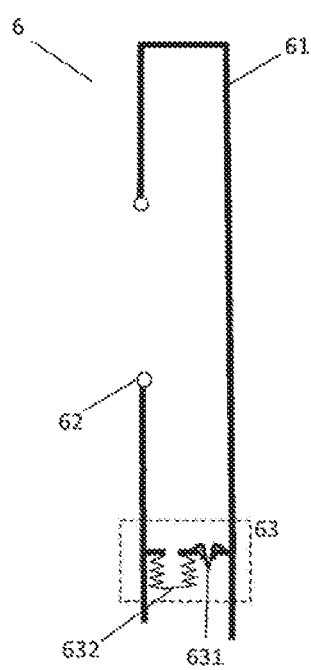
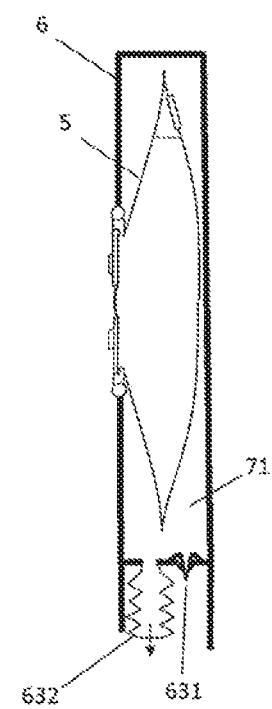
Figure 5
Figure 6
Figure 7
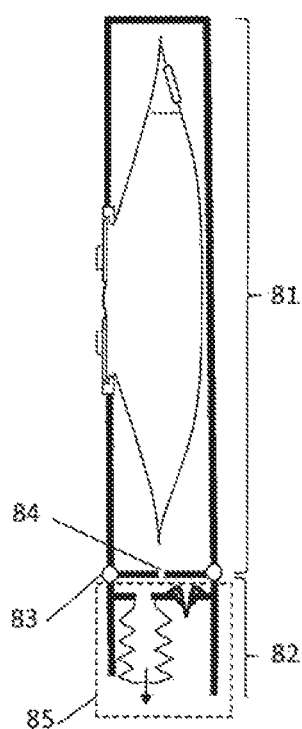
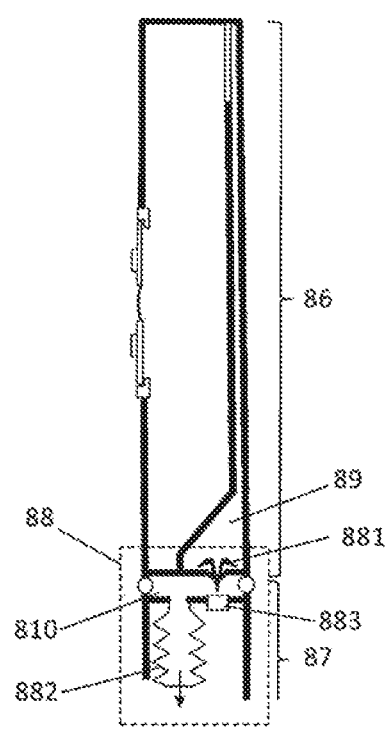
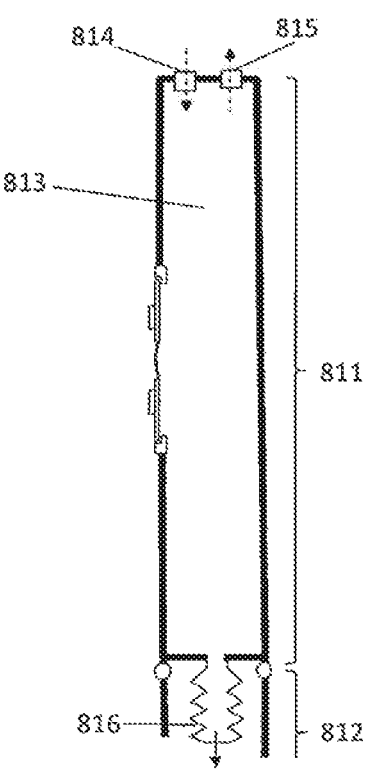
Figure 8A
Figure 8B
Figure 8C

FLUID MANAGEMENT FOR VIBRATING PERFORATE MEMBRANE SPRAY SYSTEMS

RELATED APPLICATIONS

This application is a 35 U.S.C. § 371 national stage application of PCT Application No. PCT/GB2014/052758, filed on Sep. 12, 2014, which claims priority from British Application No. 1316314.2 filed on Sep. 13, 2013, the contents of which are incorporated herein by reference in the entireties.

FIELD OF THE INVENTION

Introduction

Liquid droplet generators that make use of a vibrating perforate membrane are well known in the art with several variants used including those that vibrate the membrane directly (see U.S. Pat. No. 5,518,179 as an example) and those that vibrate a surface close behind the membrane (see WO 2009/150619 as an example). The perforate membranes in such devices are in direct contact with liquid on one side of the membrane (hereafter referred to as the back side) and, in use, atomise droplets through the perforations into a gas volume on the other side of the membrane (hereafter referred to as the front side). The gas into which the atomisation occurs is usually, but not exclusively, air at atmospheric pressure.

BACKGROUND OF THE INVENTION

It is well known in the art that these devices require the liquid pressure at the back of the membrane to be close to or more ideally slightly below the gas pressure present at the front of the membrane when in use. If liquid pressure is too high (typically greater than 2 kPa above the gas pressure at the front of the membrane but less than this for low surface tension liquids), liquid can wet out onto the front surface of the membrane leading to failure in the droplet generation mechanism. For some liquids the pressure must be below atmospheric pressure at spray commencement (typically by 0.5 kPa or more, in some cases by 2 kPa or more) as otherwise the membrane vibration process can lead to pumping of liquid onto the front surface of the membrane rather than spray generation. However if the liquid pressure is too low, gas can be drawn from the front side to the back side of the membrane which can cause a range of problems depending on the embodiment including reduced performance and foaming of the liquid. Generally too high a liquid pressure is more detrimental to device performance as compared to too low a pressure. It should also be noted that, for some applications and liquids, air is drawn back into the reservoir as droplets are ejected even if the liquid is at atmospheric pressure.

In addition to the above, such devices must also cope with natural changes in atmospheric conditions including temperature and pressure without failure either during operation or between operations. Operational failure may include reduced or no spray or leakage through the membrane. Non-operational failure may include leakage through the membrane or another interface between any liquid filled volume and the atmosphere. Surviving and working with atmospheric pressure and temperature changes is a particular challenge to portable devices, for example personal fragrance dispensers, which may be stored and used in a wide range of locations and orientations.

A further requirement of such devices, particularly those with liquid volumes that are pre-filled or used over an extended period, is to minimise liquid loss through evaporation. This is a particular challenge where the liquid to be sprayed is volatile such as an alcohol or solvent as for these liquids a significant volume can be rapidly lost if evaporation is not controlled.

There therefore exists the need for a fluid management approach that can, for vibrating perforate membrane spray devices (or devices that vibrate a surface close to the back of a perforate membrane), minimise loss through evaporation, minimise the possibility of leakage either in use or between use and ensure the liquid to be atomised is at or slightly below atmospheric pressure at the onset of atomisation. This approach should ideally be low cost to enable use in the consumer market and enable a master cartridge model so that the liquid containing component can be replaced without needing to replace the higher cost electronics components that drive the perforate membrane vibration.

Problem to be Solved

Medical and consumer perforate membrane droplet generation devices have long been in use with examples including the Pari eFlow, Omron MicroAir and Aerogen Aeroneb for drug delivery, the Panasonic EH-SM30 and PSI Nano Misty for skin conditioning and the SCJ Wisp for room fragrance delivery. These devices employ a range of fluid management approaches: Most drug delivery and skin conditioning devices have reservoirs of limited volume and require the user to manually fill this reservoir with a "dose" of fluid prior to use. This approach avoids the need to control evaporative loss or support changes in atmospheric conditions without leaking because the dose is dispensed in a short period of time and little or no liquid remains in the reservoir after use. However these devices are not suitable for longer-term use where a greater volume of fluid is stored in the reservoir and dispensed on demand over a period of days or weeks. Further, for most of these devices multi-orientation spray delivery is not possible. An example of a product having some of these limitations is the SCJ Wisp, which uses a wick to deliver fluid to the perforate membrane. This device can only operate in a narrow range of orientations, does not stop evaporation of fluid between uses, and is only suitable for supplying liquid at low flow rates.

There is a demand for perforate membrane droplet generators to be employed in devices designed for portability which need to be used multiple times in multiple orientations and where leakage of the fluid would be unacceptable. An obvious application for such a device would be body spray or fine fragrance delivery but a wide range of other applications can also be considered. In order to address this demand the liquid containment and pressure management challenges for such devices have to be solved. Existing approaches do not suffice as they all suffer from one or more of the above failure modes and would therefore be unacceptable to the user.

A portable spray device should ideally include a fluid management approach that:

1. Limits liquid loss through evaporation to an acceptable level when not in use.
2. Ensures that the likelihood of leakage between use or during use is acceptably low and that the device can be stored, transported and used in a range of environments and be subjected to typical variations in atmospheric pressure and temperature without leakage.

3. Ensures that the liquid can be successfully atomised. This can require the liquid to be at or slightly below atmospheric pressure. For some more challenging liquids this can require the liquid to be below atmospheric pressure by at least one or two kilopascals at spray commencement.
4. Enables a master-cartridge approach such that liquid-containing cartridges can be swapped or replaced without throwing away the higher-cost electronic components of the device.
5. Is low cost, low power and compact such that it is suitable for use in portable consumer or medical devices.
6. Ensures that a large fraction of the liquid contained in the cartridge can be sprayed successfully without significant change in spray performance over the cartridge life.
7. Is volume efficient—i.e. does not require the liquid reservoir to be large relative to the volume of liquid it contains.

Working under and surviving the full range of atmospheric condition changes is a particular challenge for perforate membrane spray devices as any air within the fluid reservoir will want to expand or contract based on changes in atmospheric temperature or pressure. This can lead to leakage where, for example, an increase in ambient temperature leads to a pressure increase in the reservoir and to fluid being forced out of the reservoir.

Three scenarios can be used to illustrate this. These scenarios will be infrequently seen in practice (and scenario A can be considered an extreme case) however they serve to illustrate the range of ambient changes which should ideally be supported by a device to enable it to be widely and reliably used. In scenario A a device is used under cold, sea-level conditions and next used under hot, high-level conditions. Such a scenario could be encountered if the device is packed in luggage and taken on holiday. In scenario B a device is used on an aircraft after being packed in hand-luggage at home. In scenario C a device is left in a car on what becomes a hot day. The three scenarios are summarised in Table 1 below.

TABLE 1

Considered use scenarios

| Scenario | Conditions when last used | Conditions when next to be used | ΔP if no venting | Vol expansion required |
|---|---|---|---|---|
| A | Sea level, −10° C. | 5000 ft, 35° C. | 40 kPa | 48% |
| B | Sea level, 15° C. | 8000 ft, 22° C. | 29 kPa | 38% |
| C | Sea level, 10° C. | Sea level, 50° C. | 14 kPa | 14% |

Column four of Table 1 shows the pressure increase of any air inside a fixed, sealed volume when subjected to the ambient environment change under consideration (with calculations based on using the International Standard Atmosphere). These pressures changes are much higher than the small negative pressure that is ideally required for perforate membrane device operation and would lead to leakage through the membrane rather than droplet generation if not vented prior to device use. Column five of table 1 shows the required expansion of the air that would be required to fully relieve the pressure build up. To illustrate the potential failure: if a 20 ml unvented reservoir contained 10 ml of liquid (i.e. the reservoir being half-used), almost 5 ml of this liquid could leak out under the ambient environment change of scenario A. This would be unacceptable in a product.

PRIOR ART

U.S. Pat. No. 4,533,082 teaches the use of a fan to partially evacuate air from a liquid-containing chamber in order to draw liquid up to the membrane and deliver the desirable negative pressure with negative pressure in the range 0.1 to 0.2 kPa typically achieved. This approach, whilst suitable for industrial applications, is not suitable if portability or multi-orientation use is required.

U.S. Pat. No. 5,487,378 teaches the use of a collapsible bag connected to the liquid chamber via a feed tube in which the collapsible bag has a preference to expand to maximise its internal volume. This preference can be a feature of the bag design or can result from it being placed inside a reduced pressure environment. In use this system is designed to lead to reduced liquid pressure behind the membrane. To avoid excessive negative pressure build up the bag may require periodic venting to atmosphere to allow air to enter it. U.S. Pat. No. 5,487,378 also suggests the use of a micro porous material that enables the flow of gas but not liquid for use in the removal of air bubbles from the liquid prior to entering the chamber behind the membrane. U.S. Pat. No. 5,487,378 suffers from a number of weaknesses including the need for a preferentially expanding collapsible bag (or a means for reducing pressure in the solid chamber which is not taught), the need for close timing coordination between spray commencement and the opening of the vent valve as otherwise atmospheric changes cannot be accommodated and also the bag will expand to its maximum volume after which it will not function, complex engineering, and a feed tube between the collapsible bag and chamber behind the perforate membrane.

U.S. Pat. No. 5,823,428 teaches two approaches to delivering the liquid to the membrane at a pressure below atmospheric; the use of a fluid feed comprising an open-cell capillary foam "wick" along with vent into the reservoir and the use of a small orifice 'bubble generator' that delays gas ingestion following liquid spraying until a certain pressure difference has built up. The use of a wick does not by itself solve the problems identified above and, if the wick fills the reservoir, then the sprayable fraction is poor. Bubble generators can fail if environmental changes lead to a pressure increase in the reservoir.

U.S. Pat. No. 6,581,852 utilises a flexible bag and wick approach. Whilst this has some advantages over the wick approach considered in U.S. Pat. No. 5,823,428 it requires a feed tube filled with porous media to avoid air getting back into the reservoir. This limits spray rate and is not suitable for more viscous liquids or those containing certain suspensions. U.S. Pat. No. 7,694,892 has similarities to U.S. Pat. No. 6,581,852 and suffers from similar problems including the need for a feed tube type approach. A further disadvantage of the approach presented is that a seal, used to cut off liquid supply from the reservoir to the perforate membrane to enable the reservoir to be swapped, is not directly behind the membrane leading to some evaporative loss and cross-contamination between reservoirs.

U.S. Pat. No. 6,113,001 uses a system of moving seals and changing volumes to solve many of the problems listed above. However this approach is complex and bulky, sensitive to manufacturing tolerances and hard to cost engineer.

SUMMARY OF THE INVENTION

Teaching

According to a one aspect of the invention there is provided a droplet generation device comprising a reservoir split into at least two regions by a substantially liquid impermeable barrier, a perforate membrane connecting one of said regions, containing, in use, the liquid to be dispensed, to the atmosphere, such that vibration of the membrane causes the liquid to be ejected through the perforate membrane into the atmosphere, and a pressure control system consisting of one or more valves in which at least one valve vents gas into the reservoir in response to a pressure difference, $\Delta P_{in}$, across it that is less than zero, and at least one valve is connected to a non-liquid-containing region of the reservoir and vents gas out of the reservoir in response to a pressure difference, $\Delta P_{out}$, across it that is greater than $\Delta P_{in}$, where $\Delta P_{in}$ and $\Delta P_{out}$ are the absolute pressure of the gas in the reservoir minus the absolute atmospheric pressure outside of the reservoir.

According to a another aspect of the invention there is provided a droplet generation device comprising a reservoir enclosing the liquid to be dispensed, a perforate membrane the perforations of which connect this reservoir to the surrounding atmosphere, a gas-permeable membrane also connecting the reservoir with the surrounding atmosphere wherein vibration causes liquid contained within the reservoir to be ejected in droplet form from the side of the perforate membrane exposed to the atmosphere and where the perforate membrane has been treated to make at least part of its surface hydrophobic.

According to a another aspect of the invention there is provided a droplet generation device comprising a reservoir enclosing the liquid to be dispensed, a perforate membrane the perforations of which connect this reservoir to the surrounding atmosphere, a gas-permeable membrane also connecting the reservoir with the surrounding atmosphere wherein vibration causes liquid contained within the reservoir to be ejected in droplet form from the side of the perforate membrane exposed to the atmosphere and the gas-permeable membrane performance metric kA divided by the reservoir volume V is greater than $5\times10^{-6}$ more ideally greater than $1\times10^{-5}$ where V is measured in $m^3$, A is the gas-permeable membrane area measured in $m^2$ and k is the volumetric flow velocity measured through the membrane in $m^3s^{-1}$ per unit area per unit pressure drop across it following its exposure to gas in the reservoir.

According to a another aspect of the invention there is provided a droplet generation device comprising a reservoir enclosing the liquid to be dispensed, a perforate membrane the perforations of which connect this reservoir to the surrounding atmosphere, a gas-permeable membrane also connecting the reservoir with the surrounding atmosphere wherein vibration causes liquid contained within the reservoir to be ejected in droplet form from the side of the perforate membrane exposed to the atmosphere and the gas-permeable membrane active area A divided by the reservoir volume V is greater than 0.1 more ideally greater than 1 where V is measured in $m^3$ and A is measured in $m^2$.

According to a another aspect of the invention there is provided a droplet generation device comprising a reservoir enclosing the liquid to be dispensed, a perforate membrane the perforations of which connect this reservoir to the surrounding atmosphere, a gas-permeable membrane also connecting the reservoir with the surrounding atmosphere wherein vibration causes liquid contained within the reservoir to be ejected in droplet form from the side of the perforate membrane exposed to the atmosphere and the gas-permeable membrane is a hollow tube in which the outer surface of the tube is exposed to the interior volume of the reservoir.

BRIEF DESCRIPTION OF THE DRAWINGS

The invention is now described with reference to the following drawings:

FIG. 1 is a schematic example of one aspect of the invention in which a vent plus hydrophobic coating on the perforate membrane is used to ensure pressure equalisation within a substantially rigid liquid holding reservoir.

FIG. 2 is a drawing of an exemplary embodiment of part of the container that creates the reservoir shown in FIG. 1 enabling a large vent area to be used.

FIG. 3 is a schematic example of another aspect of the invention in which a vent tube is used to ensure pressure equalisation within a substantially rigid reservoir.

FIG. 4A is a schematic example of another aspect of the invention in which a split reservoir and pressure management system is used to manage pressure behind the perforate membrane.

FIG. 4B is an alternative arrangement of the embodiment shown in FIG. 4A in which a flexible dividing layer rather than bag is used.

FIG. 4C is another alternative arrangement of the embodiment shown in FIG. 4C in which a gas-permeable membrane rather than a flexible split is used.

FIG. 5 is the cartridge part of an exemplary embodiment of the invention shown in FIG. 4A.

FIG. 6 is the master part of an exemplary embodiment of the invention shown in FIG. 4A.

FIG. 7 is the combination of the master and cartridge shown in FIG. 5 and FIG. 6.

FIG. 8A, FIG. 8B and FIG. 8C show alternative master cartridge arrangements.

FIG. 9 and FIG. 10 are plots showing venting performance for the large area vent aspect of the invention illustrated in FIG. 2.

DETAILED DESCRIPTION OF THE INVENTION

When referencing these drawings and more broadly within this specification, the following terms are used:

The term 'reservoir' is used to describe a volume that is substantially fluid tight except for the presence of one or more openings through specified parts or components. A reservoir may be formed in multiple ways and, in this specification, is used to define specific regions or volumes rather than methods of construction. A reservoir may be split into multiple secondary reservoirs or regions as described in the specification. Fluid refers, in its scientific sense, to both gas and liquid. The term 'connect' when used in relation to a reservoir refers to the creation of a fluidic pathway from the reservoir to another region. This fluidic pathway may go through one or more other components of features in series with the component or feature that the term 'connect' is being applied to such as a wick, a piece of porous media or a tube.

The term 'rigid' when applied to a reservoir, region or component that creates such (e.g. a component that splits a reservoir into two regions) means that the reservoir, region or component referred to does not substantially deform (i.e. increase or decrease in volume or moves to increase or decrease the volume of a connected reservoir or region)

when subjected to the range of differential pressures experienced in normal use. For example a rigid reservoir will ideally support pressure differences as great as 5 kPa or more between its interior and exterior and certainly as great as 1 kPa. For clarity some deformation of a rigid reservoir or region may occur but such deformation will not be great enough to lead to the pressure difference between the interior and exterior dropping below the above values.

The term 'flexible' when applied to a reservoir, region or component that creates such (e.g. a component that splits a reservoir into two regions) means that the reservoir, region or component referred to deforms when subjected to a low differential pressure across it (i.e. a low pressure between the interior and exterior volume of the reservoir or region or a low pressure across the component). Such deformation will ideally keep the pressure difference to no more than 1 kPa. For clarity a flexible reservoir or region will no longer behave in this way if it is sealed or if it is substantially empty or if all of the surfaces of the reservoir are already in tension (i.e. the container has already expanded to its maximum volume) and a component will not behave in this way if it is already all in tension or constrained from deforming by another structure. In this specification a reservoir or region is still classed as flexible when it has a slight preference to collapse.

'Master' and 'cartridge' refer to two distinct parts which together form a usable device. The master unit is intended to be reusable and contains high value components such as the battery and drive electronics and possibly also the actuator, while the cartridge is intended to be disposable and contains at a minimum the liquid to be sprayed. Both the master and the cartridge may include one or more reservoirs and pressure management components as referred to in the various embodiments of this invention. Some reservoirs or regions may only be formed when the master and cartridge components are assembled together.

The term 'gas-permeable membrane' as used herein means a component or material that allows gas but not liquid to flow through it. It may by hydrophobic or oliophobic depending on the application and the liquid under consideration. Examples of gas-permeable membranes include ePTFE material from WL Gore and ePTFE tubing from Zeus Inc. The cracking pressure of the gas-permeable membrane (i.e. the pressure difference at which the liquid will pass through the gas-permeable membrane and cause it to fail) will vary for different applications. The terms 'hydrophobic' and 'oliophobic' are used interchangeably and in this specification and refer to the repelling of the liquid to be dispensed.

The term 'pressure control system' means a system used to manage the pressure within a reservoir relative to local ambient pressure that includes, at a minimum, the ability to both release gas from and allow gas into the reservoir based on the pressure difference across the pressure control system (i.e. the pressure difference between the reservoir and the surrounding atmosphere). These gas flows may be controlled by one or more valves which may be arranged to allow flow in opposite directions. In some embodiments the pressure control system may also include a component that actively changes the volume of the reservoir being managed or actively draws gas out of the reservoir. Where this is the case the pressure control system may include features that drive this volume change or gas removal.

One embodiment of the invention, suitable for use with liquids that need to be close to atmospheric pressure at spray commencement, is disclosed in FIG. 1. In this embodiment a rigid reservoir volume (12) is designed to be substantially filled with liquid prior to initial use. This liquid is, in use, ejected in the form of droplets through the perforate membrane (13) where such perforations may be tapered such that the diameter of the orifice at the back surface of the mesh is of larger diameter than the diameter of the orifice at its front surface. The perforate membrane is vibrated in use by an actuator (14). In this instance the actuator vibrates the membrane directly and is of the "bending mode" type known in the art although other types of actuators may also be used including those whose motion is broadly radial ("breathing mode" actuators) and those whose motion is broadly axial ("thickness mode" actuators). Further, rather than vibrating the perforate membrane directly a plate broadly parallel to and close to the membrane inside the liquid filled reservoir may be vibrated instead. A range of actuator constructions can be considered including actuators that use a piezo-electronic (PZT) material as an active element. The membrane may be permanently bonded to the actuator through adhesive, welding, soldering or other methods. Alternatively the membrane may be removable from the actuator with connection through magnetic, bayonet, push-fit, sprung or other methods. In the present embodiment the actuator is of bending mode type made through adhesive bonding of a ring of PZT material to a substrate. The membrane is welded or adhesively bonded to the substrate. In use an alternating voltage is applied across the PZT layer using drive electronics not shown in the figure. The actuator (14) is mounted into a container (11) using a low shore hardness material such as a thermoplastic elastomer (TPE) (15) that provides a fluid tight seal, good barrier properties to vapour and gas permeation and does not significantly damp actuator vibration. Other materials that provide the above elastomeric properties can also be used including rubber-based compounds and some silicones. Alternative mounting approaches include the use of flexible films of materials such as PET and Kapton or films manufactured with more than one layer to produce the right balance of properties. In the present embodiment the actuator (14) forms part of the reservoir surround although this does not have to be the case.

A fluid feed comprised of a porous medium such as open-cell foam (16) can be optionally included within the reservoir volume to maintain the feed of liquid to the back of the perforate membrane as the bulk liquid level drops and to enable all-orientation spray delivery. It should be noted that the purpose of this foam is simply to maintain the feed of fluid to the head, and it is not necessary to have a feed tube or equivalent as required in for example U.S. Pat. No. 6,581,852 (i.e. an extended element comprised of porous media that the liquid must flow along) connecting the reservoir to the perforate membrane. (Such elements are used in the prior art in order to provide flow resistance and thereby to reduce the pressure of the liquid at the back of the membrane). The ability for the spray head to be directly connected to the reservoir is a benefit of this invention over the prior art as it enables increased spray rates and reduced complexity.

To enable air to be vented if atmospheric temperature increases or pressure falls a gas-permeable membrane (17) combined with an optional evaporation-limiting path (18) is used. The pathway (18) is long and thin to reduce liquid loss through diffusion of vapour and may be serpentine in nature. An optional seal (19) is also used to limit evaporation through the perforate membrane and to stop leakage if a significant pressure difference does build up. The seal may be a lip seal of the type shown in the figure and may seal onto the membrane, the actuator or another component.

Further, if the porous medium (16) is not used the seal could be of the "back face" type as described in EP2293882. Back face seals in which the seal resides between the membrane and porous medium when sealing and then moves out of the way may also be useable.

Whilst the use of a gas-permeable membrane enables the device to continue functioning even when subjected to large atmospheric condition changes it does introduce two drawbacks that in some circumstances will need to be compensated for.

Figure 4A:
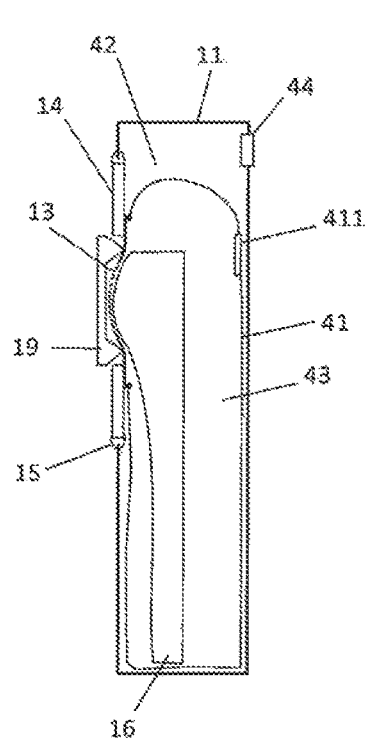
Figure 4B:
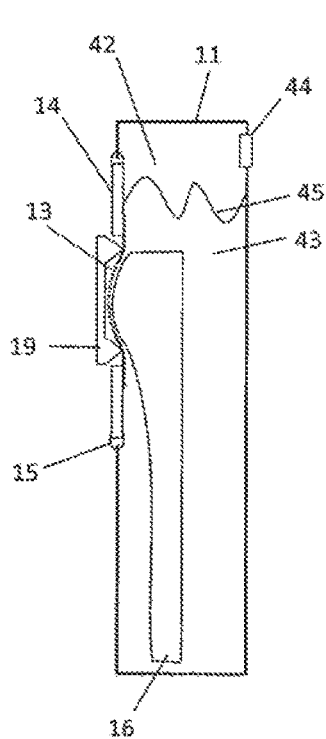
Figure 4C:
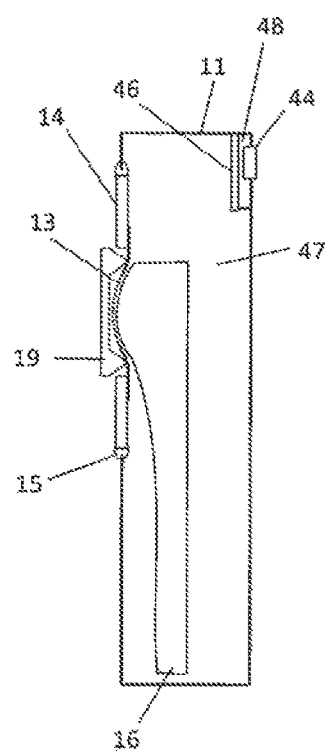

The first is that such gas-permeable membranes generally let vapour through relatively easily therefore creating a route for evaporative loss. This can be overcome by placing a long thin diffusion limiting path on the side of the gas-permeable membrane away from the liquid side. This diffusion limiting path (18) can be serpentine in nature to enable its length to be maximised. An alternative approach is shown in FIG. 4C in which the diffusion limiting path is replaced by a pressure control system (44). This pressure control system, which can avoid the second drawback of the approach as discussed below, is discussed more broadly later in this specification.

The second drawback is that in general and for low surface tension fluids in particular, the presence of a second pathway from the atmosphere into the rigid reservoir can lead to liquid seeping out of the perforate membrane if the bulk liquid level is above that of the perforate membrane, the perforate membrane is unsealed and the perforate membrane is not being vibrated. This seepage can occur because if the fluid unpins from any one of the nozzles or perforations there is nothing to constrain continual liquid flow. The authors have though found that the use of a hydrophobic coating on the perforate membrane can stop this failure mode. If some liquid is left on the front surface of the perforate membrane then it may form a drop and fall off but, if coated with a hydrophobic layer, this does not lead to continued seepage. A range of coatings have been considered and tested and ultra thin polymer nano-coatings that significantly lower the surface energy of the perforate membrane surface have been shown to work well. In an ideal embodiment such coatings would only be applied to the front surface of the perforate membrane but coating all surfaces of the perforate membrane including inside the perforations or nozzles has also been shown to work.

As the reservoir may be initially substantially liquid filled and the device may be stored in any orientation there may be times when the gas-permeable membrane is fully liquid-covered and therefore not able to function as a gas vent. During these periods the pressure in the reservoir could rise substantially above that of the ambient atmosphere as illustrated in column four of Table 1. The gas-permeable membrane must not fail mechanically or "crack" under these pressures (i.e. begin to transmit liquid) and nor must the perforate membrane seal fail. Further, pressure in the reservoir must be substantially equalised with the atmosphere before the perforate membrane seal is removed and the device used. This could be achieved by locating multiple gas-permeable membranes within apertures in the reservoir walls (ideally one at each corner) or by only partially filling the reservoir (ideally to less than half full). Neither of these approaches is preferred due to the resulting cost or size increase. Therefore it is preferable that the gas-permeable membrane is located such that it is able to vent the reservoir under a range of normal use orientations, and sized such that pressure equalisation occurs rapidly, i.e. before the user operates the device. In this way pressure equalisation can occur before the perforate membrane seal is removed, avoiding leaking through the perforate membrane, and the pressure within the reservoir can be within the range necessary to achieve droplet production.

It is important to recognise that, for most devices, the operator will naturally hold the device in a certain orientation for a period before commencing spraying. For example a body spray device may be used in many orientations in order to deliver droplets all over the body but it will likely be held in an upright orientation for opening prior to spraying. In this situation the gas-permeable membrane should be located at the top of the device so that the reservoir is vented when the device is oriented in its standard design orientation prior to spraying. For devices where the possibility of leakage or spray failure cannot be tolerated even exceptionally then features that warn the user or more ideally disable seal opening or spray commencement if pressure has not been equalised can be included. Such features could be passive, for example the perforate membrane seal could be locked shut by a deformable wall on the reservoir or a component that is exposed to the pressure difference seen across the perforate membrane.

In calculating the required gas-permeable membrane area, speed of venting must be considered. Modelling flow through the gas-permeable membrane as proportional to the pressure difference across it and using the First Law of Thermodynamics to consider the venting process leads to the following differential equation:

$$\frac{dp}{dt} + \gamma k \frac{A}{V} p(p - p_\infty) = (\gamma - 1)\frac{hA_T}{V}(T - T_\infty) \qquad \text{Equation 1}$$

Considering the left hand side of the equation first, p is the reservoir pressure, $p_\infty$ is the atmospheric pressure, A is the active area of the gas-permeable membrane, V is the volume of gas in the reservoir and $\gamma$ is the gas constant (equal to 1.4 for air). k is a measure of the gas-permeable membrane performance in terms of gas volumetric flow through the membrane per unit membrane area per unit pressure difference across it (units of $m^3$/Ns). Equation 1 assumes that the gas flows through the membrane at the density it is in the reservoir whereas in practice the density will vary through the membrane. The impact of this assumption is relatively small as the density variation of the gas under consideration is small.

The left-hand side of the above equation is a statement of conservation of energy with the pressure reducing as gas escapes through the membrane. As this process occurs the gas remaining in the reservoir will cool and therefore heat will be absorbed from the environment adding energy. This energy addition is described by the right-hand side of the equation where T is the reservoir gas temperature, $T_\infty$ is the surrounding temperature (including that of the liquid in the reservoir), $A_T$ is the area heat is transferred across and h is the convective heat transfer rate in W/$m^2$K. The gas pressure and temperature can be related by the perfect gas equation pV=mRT where R is the gas constant (equal to 287 J/kgK for air) and m is the mass of gas remaining in the reservoir.

Equation 1 can be solved iteratively to predict how long it will take the pressure in the reservoir to fall below a set value following the commencement of venting. This is illustrated in FIG. 9 which is an example of the venting process for Scenario B described above in which the starting pressures and temperatures are as described in the user scenario, V=10,000 $mm^3$, A=100 $mm^2$, $k=2.5\times10^{-6}$ $m^3$/Ns, h=10 W/$m^2$K and $A_T$=100 $mm^2$. In this figure the solid line is the pressure difference across the gas-permeable membrane and the dashed line is the temperature of the gas remaining in the reservoir. It should be noted that the values of V, h and $A_T$ listed above are considered reasonable for a portable consumer spray reservoir, A equates to a circular vent of 11 mm diameter which is large compared to the 10 ml of air in the reservoir and the venting rate, k, is representative of test data for a high performing vent for low surface tension fluids with suitable cracking pressure such as those available from WL Gore. Published figures for such vents have k ranging from $8 \times 10^{-5}$ m$^3$/Ns down to $4 \times 10^{-6}$ m$^3$/Ns but the authors have found that when used for rapid venting in practice after being wet with the liquid k values are often less than the published values.

Figure 9:
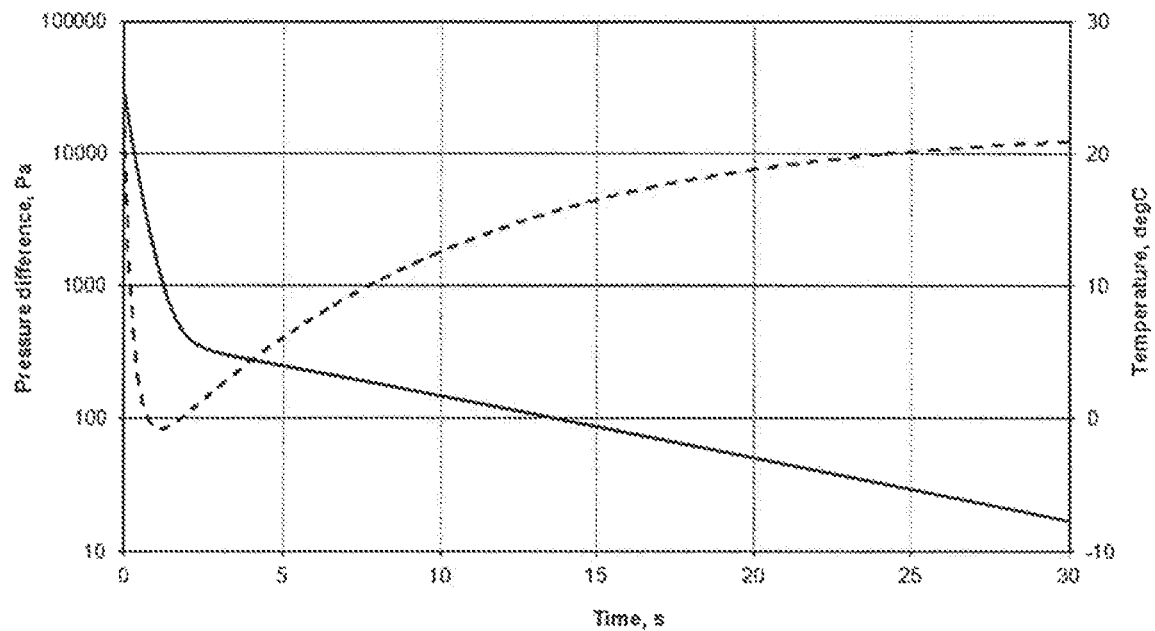
Figure 10:
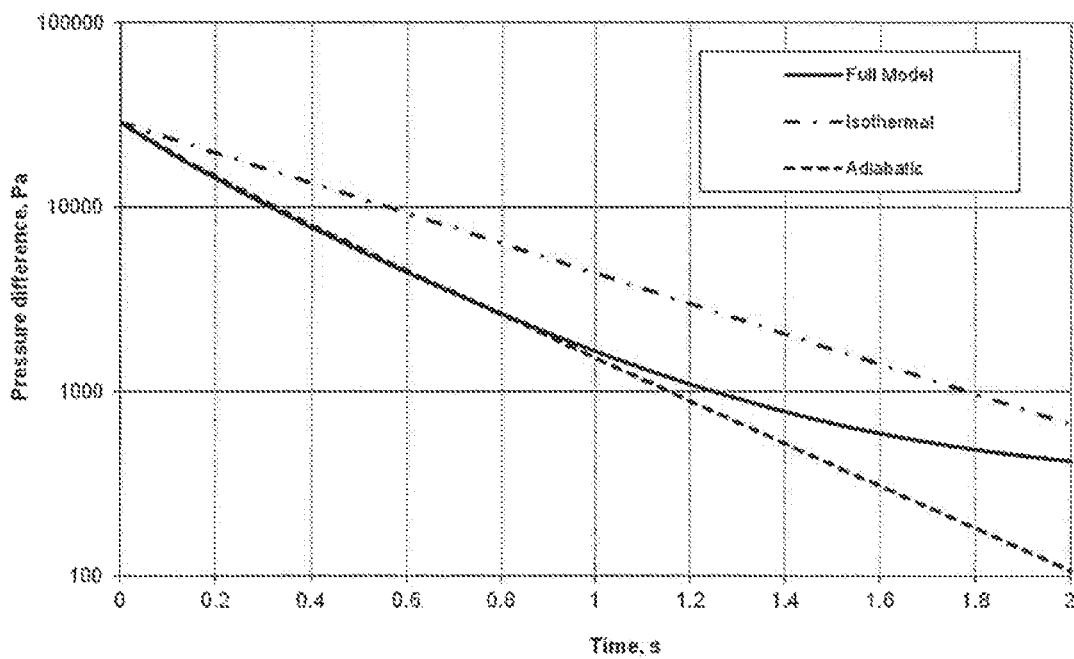

In FIG. 9 it can be seen that, due to the large vent area, pressure falls rapidly at first before a second slower rate of equalisation is established. This two stage process is linked to the cooling and subsequent warming of the gas back up to atmospheric temperature. For the application considered here device operation requires cartridge pressure to be no more than ~1 kPa above atmospheric pressure prior to perforate membrane seal removal and spray commencement otherwise leakage and/or spray failure may occur. FIG. 10 shows the drop to below this pressure value in more detail alongside two simplifications in the model; one assuming the venting is adiabatic (i.e. no heat transfer) and one assuming the process is isothermal (i.e. heat transfer is quick enough to keep the gas temperature constant). As expected the adiabatic simplification underestimates venting time down to 1 kPa whilst the adiabatic process overestimates it. The equations for the two simplified processes are shown below:

$$\frac{kA}{V} = \frac{1}{T}\frac{1}{p_\infty}\ln\left[\frac{\Delta p_0}{\Delta p_1}\frac{p_\infty + \Delta p_1}{p_\infty + \Delta p_0}\right] \quad \text{Equation 2(isothermal)}$$

$$\frac{kA}{V} = \frac{1}{\gamma}\frac{1}{T}\frac{1}{p_\infty}\ln\left[\frac{\Delta p_0}{\Delta p_1}\frac{p_\infty + \Delta p_1}{p_\infty + \Delta p_0}\right] \quad \text{Equation 3(adiabatic)}$$

In the above equations, T is the time venting has occurred for, $\Delta p_0$ is the pressure difference across the gas-permeable membrane at the start of venting (i.e. T=0) and $\Delta p_1$ is the pressure difference across the gas-permeable membrane at the end of venting after time T.

Unlike equation 1 which needs to be solved iteratively, these equations can be used directly to provide estimates of the required gas-permeable membrane performance metric kA per unit reservoir gas volume V. Results of this are shown in table 2 below for the three scenarios under consideration when looking to vent down to a 1 kPa pressure difference within one or two seconds. Based on this table and considering that the user cases are considered worst case, the gas-permeable membrane performance metric kA per unit reservoir volume V should be greater than $5\times10^{-6}$ more ideally greater than $1\times10^{-5}$, and even more ideally greater than $2\times10^{-5}$ to deliver rapid cartridge venting.

TABLE 2

Gas-permeable membrane performance criteria

| Scenario | T = 1 s | | T = 2 s | |
|---|---|---|---|---|
| | kA/V (eq. 2) | kA/V (eq. 3) | kA/V (eq. 2) | kA/V (eq. 3) |
| A | $3.9 \times 10^{-5}$ | $2.8 \times 10^{-5}$ | $2.0 \times 10^{-5}$ | $1.4 \times 10^{-5}$ |
| B | $4.1 \times 10^{-5}$ | $2.9 \times 10^{-5}$ | $2.0 \times 10^{-5}$ | $1.4 \times 10^{-5}$ |
| C | $2.5 \times 10^{-5}$ | $1.8 \times 10^{-5}$ | $1.2 \times 10^{-5}$ | $0.9 \times 10^{-5}$ |

Considering the various values in membrane material performance value, k, discussed above, the value of vent area A to reservoir volume V should ideally be greater than 0.1, more ideally greater than 1, and even more ideally greater than 5. For both kA/V and A/V, the ideal value will vary depending on acceptability of occasional failure and the liquid to be sprayed. Using low surface tension liquids that must not leak will lead to the requirement for higher values of kA/V and A/V. Conversely the use of high surface tension liquids in which occasional leaks are seen as acceptable (e.g. water) will lead to lower values of kA/V and A/V being acceptable.

In the above limits and bounds the value of A is the active area of the membrane and the value of k is that measured just after the liquid in the reservoir is removed from the membrane surface by, for example, re-orientation of the reservoir. As a large area vent and a long diffusion path are ideally required for such devices, FIG. 2 shows a 3$^{rd}$ angle drawing of a preferred embodiment of these features into a half of the container that is used to form the rigid reservoir (21) suitable for manufacture with a simple mould tool. A fill port (22) is included along with a recess (23) that defines the gas-permeable membrane active area, A. The gas-permeable membrane itself is ultrasonically welded or bonded through some other means along the line (24). A through port (25) is used to connect the space behind the gas-permeable membrane to the diffusion path (26) which ends in an opening (27). To complete this diffusion path a foil label or similar material with low vapour transmission rate is bonded to the back of the part (21) such that the fill port and serpentine path are sealed and just the opening (27) is exposed to the atmosphere.

FIG. 3 shows another embodiment of the invention in which, instead of a large area gas-permeable membrane, a long extruded gas-permeable membrane (31) is used. The advantage of such an approach is that it will in most circumstances remain in contact with any gas in the rigid reservoir. Gas-permeable membranes located at all corners of the reservoir are not required reducing cost and simplifying assembly. This approach also has the advantage that a pressure difference will not build up in the reservoir enabling a gas-permeable membrane with a lower cracking pressure to be used and a simpler perforate membrane seal. Extruded ePTFE tube sealed at one end is well suited to this application although alternative long thin gas-permeable membrane structures may also be used. The structure may be left free to find its own position in the reservoir or alternatively routed through the use of guides or clips of connected to a float. With a second path between the reservoir and atmosphere present (unless the pressure control system approach (44) as shown in FIG. 4C is used), hydrophobic coating of the perforate membrane is desirable and required to avoid seepage in some embodiments. Variations on the approach discussed in relation to FIG. 1 are also applicable here such as the use or otherwise of a porous open cell foam and the use of various actuator types.

The embodiments discussed above are well suited to applications in which the liquid must be close to but not necessarily below atmospheric pressure at spray commencement. Some liquids, particularly those with increased viscosity, must though be supplied to the back of the perforate membrane at a pressure below the atmospheric pressure seen on the front surface of the membrane at spray commencement. Such liquids may include, but are not limited to, certain skin conditioning formulations, paints, highly particle loaded liquids and glycols. For these liquids a fluid management approach that always ensures fluid behind the perforate membrane is at negative pressure at spray commencement is required. The ideal negative pressure difference will vary for different liquids. In some cases it has been shown that the liquid should be at a pressure value 1 kPa±0.5 kPa below atmospheric gas pressure to deliver reliable controlled droplet ejection. In other cases more negative pressures have been used, in some cases more than 2 kPa below atmospheric gas pressure. As the pressure difference becomes too negative air can be ingested into the liquid space behind the perforate membrane either continuously or during spraying. For some embodiments and liquids this must be avoided but for some embodiments and liquids this is acceptable.

FIGS. 4A, 4B and 4C illustrate various embodiments of the invention that can ensure liquid pressure behind the perforate membrane is below atmospheric pressure.

In FIG. 4A a flexible reservoir volume (43) is created through the use of a flexible bag or equivalent (41) in which this flexible bag is, at a minimum, substantially liquid impermeable under the conditions of use. This flexible reservoir (43) is housed within a rigid reservoir volume (42) created through the use of one or more rigid components (11) including in this instance the actuator (14). The flexible bag or equivalent can be considered as dividing the rigid reservoir into two regions. All the variations described in relation to FIG. 1 are applicable here including without limitation various actuator types, the use of a wick or open cell foam, sealing and mounting means. However it should be noted that an advantage of the use of a flexible bag or equivalent that collapses as liquid is sprayed is that liquid remains behind the perforate membrane even if the membrane is above the bulk of the liquid on first use. The flexible reservoir volume (43) is ideally substantially liquid filled on first use and its only direct liquid permeable connection to the atmosphere outside of the rigid volume is through the perforate membrane. The connection between the bag forming the flexible reservoir and the perforate membrane may be direct as shown in the figure or could instead be via a secondary component such as the actuator or a plastic mount. In all embodiments the flow of liquid from inside the perforate membrane contacting reservoir to the second gas filled reservoir is not possible under normal use conditions. Gas flow may though be enabled between these two reservoirs either through the use of a gas-permeable membrane (411) or through the choice of flexible bag material or construction. For example the flexible bag could itself be a gas-permeable membrane or the flexible bag could have several small holes in it such that liquid pins in the holes and does not flow between the volumes but gas can flow. If a gas-permeable membrane or equivalent is used then in normal use conditions, liquid will not crack the membrane or flow between the reservoirs because the pressure difference between the two reservoirs is kept small due to the bag being flexible. The advantage of enabling gas flow between the reservoirs or regions is that it enables air to be ingested through the perforate membrane during operation without possibly leading to device failure. To encourage air removal from the liquid filled reservoir it may, in some embodiments, be desirable to use a flexible structure that has a slight preference to collapse the reservoir in contact with the perforate membrane, such that gas inside this liquid containing reservoir is at a pressure slightly above that of gas inside the gas filled second reservoir.

A pressure control system (44) is used to regulate the pressure in the rigid volume and hence also the pressure in the flexible volume. This pressure control system may consist of one or more components located together or in separate positions linking the rigid volume to the atmosphere. This pressure control system has, at a minimum, the following features; it will allow gas to leave the rigid volume if pressure in the rigid volume differs from atmospheric pressure by a certain amount, $\Delta P_{out}$ and it will allow gas to enter the rigid volume if atmospheric pressure differs from atmospheric pressure by a certain amount, $\Delta P_{in}$. In this description both $\Delta P_{out}$ and $\Delta P_{in}$ are the absolute pressure of the gas in the rigid reservoir minus the absolute atmospheric pressure. In an ideal embodiment the pressure control system is passive and $\Delta P_{out}<0$ ideally $\Delta P_{out}<-0.5$ kPa and $\Delta P_{in}<\Delta P_{out}$ ideally with the difference between $\Delta P_{in}$ and $\Delta P_{out}$ being no more than 1 kPa (i.e. the pressure control system will keep the pressure in the rigid reservoir below atmospheric pressure between two close together limits). However such a passive pressure control system is not possible in practice as work must be done to force air out of the rigid reservoir if $\Delta P_{out}<0$. Therefore in practice $\Delta P_{out}$ should be low but this is likely to be greater than or equal to zero, for example $\Delta P_{out}<+0.1$ kPa. $\Delta P_{in}$ should be set to less than zero, ideally to the ideal negative pressure for the liquid, i.e. $-0.1$ kPa$>\Delta P_{in}>-10$ kPa, more ideally, $-0.5$ kPa$>\Delta P_{in}>-2$ kPa although this range depends on the liquid as discussed earlier. With $\Delta P_{in}$ and $\Delta P_{out}$ operating in these ranges reservoir pressure is constrained between two limits but operation at negative pressure is not guaranteed as $\Delta P_{out}\geq 0$. Therefore in a preferred embodiment the pressure control system also includes an active component that is used to draw air out of the rigid reservoir or increase its volume before spray commencement.

This active component may be a syringe, baffle or some other device that acts to increase rigid reservoir volume (including a controlled deformable wall of the reservoir) or it may be a gas pump. The activation of this active component is preferably linked to the removal of a seal over the perforate membrane by the user, for example the motion to remove the perforate membrane seal also leads to the rigid reservoir volume being increased or some air being forced out of the rigid volume. With other elements of the pressure control system limiting pressure difference to being less than $\Delta P_{out}$ and greater than $\Delta P_{in}$, this volume change/gas removal feature does not need to be well controlled as, if excess air is removed or the volume increased more than required the rigid reservoir pressure will not drop below $\Delta P_{in}$ relative to atmospheric pressure. In this configuration the pressure control system will at all times constrain rigid reservoir pressure between $\Delta P_{in}$ and $\Delta P_{out}$ and force the rigid reservoir pressure to below atmospheric pressure (capped at $\Delta P_{in}$) just prior to spray commencement. This approach enables reliable delivery of challenging liquids through the use of simple mechanical components.

The elements of the pressure control system that control the flow of gas into and out of the reservoir in response to the pressure difference as discussed above are, in a preferred embodiment passive and formed using one or more valves. Suitable valves include flap, duck-billed, umbrella, ball, dome and cross-slit. Two valves can be used each controlling flow in one direction or a combination valve (e.g. umbrella plus duck-bill) can be used to control flow in both directions. For the valve component controlling $\Delta P_{in}$ the valve will ideally be sealed substantially tight when the pressure difference across it is zero. For the valve controlling $\Delta P_{out}$ though the valve could be non-sealed at zero pressure difference (i.e. it has no cracking pressure). Such valves typically allow flow in both directions when the pressure difference across them is very low. The advantage of using a zero-cracking pressure valve is that it will enable $\Delta P_{out}=0$. The disadvantage is that, because they enable some flow in both directions under low pressure differences the active component of the pressure control system must operate quickly enough such that a negative pressure can be established and the valve enabling air flow out of the device sealed to reverse flow. In some embodiments it may be preferable for the components enabling gas flow in response to pressure difference to be active rather than passive or constrained from opening under certain conditions. For example an active valve could be opened in response to the pressure difference sensed by a transducer.

Once spraying has commenced then perforate membrane devices may maintain their negative pressure as liquid is being removed from the reservoir. However for some very challenging liquids where high negative pressure is required and constant air ingestion during spraying results, pressure may need to be maintained at a value below that that the device can self-sustain. In these instances the active element of the pressure control system may need to continuously remove gas from the rigid volume. This gas removal rate can be higher than is needed with the passive element of the pressure control system allowing air back into the rigid reservoir maintaining the pressure difference close to $\Delta P_{in}$. In the above descriptions and discussions the valves and reservoirs are ideally sealed except as described. However in some instances small leaks or back flows may occur and the invention described here is intended to capture such embodiments so long as the leaks or back-flows are small enough such that they do not alter the fundamental operation of the features described herein.

The embodiment illustrated in FIG. 4B is an adaption of the approach outlined above in relation to FIG. 4A. Instead of a flexible bag (41) being used to split the rigid reservoir into two secondary reservoirs or regions a flexible surface (45) is used instead. This surface may have the same properties as described for the bag and may include a gas permeable portion or component. The flexible surface acts, like the flexible bag, to separate the rigid reservoir into two regions one substantially liquid containing on first use and in contact with the perforate membrane (13) and one gas containing and in contact with the pressure control system (44). The flexible surface like the flexible bag may be mounted in several ways including heat staking, bonding or welding to the components that make up the structure of the rigid reservoir.

The embodiment illustrated in FIG. 4C combines some of the features and benefits of the embodiments illustrated in FIG. 1 and FIG. 4A. A gas-permeable membrane (46) is used to split the rigid reservoir into two rigid reservoirs (47) and (48). The reservoir in contact with the perforate membrane (47) is liquid and gas containing whilst the second reservoir (48) is gas containing. The pressure control system (44) operates in contact with the second rigid reservoir (48) as described earlier with the same range of variants and embodiments possible. The advantages of this approach over that illustrated in FIGS. 4A and 4B is that a flexible bag or surface is not required. This may reduce manufacture costs and can improve aesthetic appearance. A disadvantage is that a wick or porous media is more likely to be required to deliver all-orientation spray and enable the perforate membrane to be above the bulk of the liquid on first use. A second disadvantage is that the pressure control system may fail to regulate pressure in the liquid filled reservoir (47) if the gas-permeable membrane is liquid covered. A third disadvantage is that even if not liquid covered the gas-permeable membrane will provide a resistance to gas flow that could disrupt the performance of the pressure control system in some circumstances. The second of these disadvantages can be overcome through the use of a gas permeable tube or equivalent (31) as illustrated in FIG. 3 instead of the gas-permeable membrane (46) to connect the two rigid reservoirs together.

Whilst the pressure control system can be used to deliver a negative pressure at spray commencement the use of a hydrophobic coating on the perforate membrane as described in relation to FIG. 1 may still be beneficial in some instances.

FIGS. 5, 6 and 7 illustrated a preferred embodiment of the invention in which the device is separated into master and cartridge components. The cartridge component (5) is illustrated in FIG. 5 consisting of a liquid containing flexible reservoir (56) possibly but not necessarily with some air in (57) created using a flexible bag (55) bonded to a support ring (54) in which is flexibly bonded an actuator consisting of substrate (51) and PZT ring (52). A domed perforate membrane (53) is bonded to the substrate. In this instance the perforate membrane was made of electroformed nickel in which the nozzle exit diameter was 16 microns but the general approach is suitable for a wide range of actuator types, perforate membrane materials (including steel and kapton), perforate membrane shapes (domed and flat) and nozzle sizes (from <1 um exit diameter up to >100 um exit diameter). A perforate membrane seal (59) is used to seal the perforate membrane to limit evaporative loss and a gas-permeable membrane (58) may be included depending on the application. This cartridge has multiple advantages including being aesthetically pleasing by itself and simple to construct without any of the pressure control system components on it. In the embodiment shown here the cartridge includes the actuator component but the approach outlined here is readily adaptable to moving the actuator to the master leaving only the perforate membrane in the cartridge as outlined in WO2012/156724 incorporated herein for reference. This removes additional cost from the cartridge increasing the benefit of the approach.

The master component (6) is illustrated in FIG. 6. This includes the pressure control system (63), a rigid structure (61) and a sealing surface (62). The pressure control system in this embodiment incorporates a combined umbrella and duck billed valve (631) in which the umbrella portion of the valve regulates gas flow into what will become the rigid reservoir and the duck-billed portion of the valve regulates gas flow out of what will become the rigid reservoir. The pressure control system also includes a plunger component (632) that is actively used to alter the volume of what will become the rigid reservoir.

In use, the master (6) and cartridge (5) components are assembled together as shown in FIG. 7. The sealing surface (62) of the master component seals to the support ring (54) of the cartridge creating a rigid reservoir (71) that includes the flexible reservoir (56) within it. In use, the perforate membrane seal (59) is removed and the active component of the pressure control system (632) actuated so as to ensure the liquid behind the perforate membrane is at negative pressure just prior to spray commencement. This beneficial split enabling a master-cartridge approach in which the key pressure control components are included in the master component may also be extended to the other embodiments previously discussed. Referring to FIG. 4B the flexible surface (45), liquid containing reservoir (43) and perforate membrane (13) may form part of the cartridge with the second reservoir (42) created on assembly of this cartridge to or into the master unit. Referring to FIG. 4C the gas-permeable membrane (46), liquid containing reservoir (47) and perforate membrane (13) may form part of the cartridge with the second reservoir (48) created on assembly of this cartridge to or into the master unit.

FIGS. 8A, 8B and 8C illustrate three alternative master-cartridge embodiments of the invention. In FIG. 8A the cartridge (81) consists of the flexible reservoir and a rigid outer shell with an opening (84). In use this cartridge is connected to the master unit (82) at sealed join (83) thus creating the rigid reservoir that is connected to the pressure control system (85). This embodiment enables the cartridge component to be rigid whilst keeping the pressure control components in the master. The opening in the cartridge (84) may be adapted to limit evaporative loss when the cartridge is not connected to the master unit. This includes making the opening a diffusion limiting path and using a valve across the opening that either opens when the master and cartridge units are connected or open at pressure differences less than the primary valves that form part of the pressure control device.

In FIG. 8B the cartridge component (86) consists of two rigid reservoirs of the type outlined in the discussion relating to FIG. 4C. In this embodiment the pressure control system (88) is split across the master and cartridge with the passive components (881) in the cartridge and the active components in the master. This approach requires a more complex active component to the pressure control system consisting of a volume change component (882) and a valve that can be opened or shut actively (883) this valve is open when not spraying to enable pressure in the reservoir to be limited and is closed just before the volume change component (882) is activated. This approach is not preferred as it adds complexity to the solution and requires better control of volume change but should be considered as within the scope of this invention with the pressure in the rigid reservoir (89) still controlled by the pressure control system (88).

In FIG. 8C a non preferred embodiment of the invention is illustrated. The cartridge (811) comprises a rigid fluid filled reservoir (813) with three components of the pressure control system (814, 815 and 816) connected to it. Part 814 is an inlet valve that allows atmospheric gas into the reservoir. Part 815 is an exit valve that allows gas out of the reservoir. To avoid liquid flowing through part 815 a gas-permeable membrane must be incorporated within it (unless it has been separated from the rest of the reservoir by a gas-permeable membrane). Part 815 therefore in practice consist of two components separated by a small but defined gas filled reservoir: The gas-permeable membrane component of part 815 connects the gas filled reservoir region within part 815 to the liquid filled reservoir (813) and the pressure control components of part 815 connect the gas filled reservoir region within part 815 to the atmosphere. A bellows system (816) also forms part of the pressure control system which in use deforms to increase reservoir volume just prior to spray commencement. The liquid contacting component of the bellows component in this embodiment forms part of the cartridge but is actuated by a part of the master and therefore the pressure control system is considered to reside in both the master and cartridge components. In this embodiment this active part of the pressure control system is connected to the liquid filled reservoir rather than the gas filled reservoir which is non-preferred but encompassed within the scope of the invention.

The above described invention, descriptions and embodiments are primarily related to the use of a rigid reservoir. However they can also be applied to a non-rigid reservoir if the non-rigid reservoir behaves like a rigid reservoir under some circumstances (e.g. when subjected to larger than usual atmospheric pressure changes). They can also be applicable and useful if the reservoir does not deform until a certain pressure difference has built up as the pressure control system can then avoid the reservoir deforming in most circumstances but deformation can be used as a back-up if the gas-permeable membrane is, for example, blocked by liquid. For example the reservoir can be designed to expand if the pressure difference becomes much greater than $\Delta P_{out}$.

It should be understood that the embodiments included in this specification are non-limiting and should be considered as illustrations as to the scope of the invention.

The invention claimed is:

1. A droplet generation device comprising:
   a rigid reservoir split into at least two regions by a barrier that consists, at least in part, of a gas-permeable membrane that is substantially liquid-impermeable and has a performance metric kA divided by the reservoir volume V that is greater than $5 \times 10^{-6}$ where V is measured in $m^3$, A is the gas-permeable membrane area measured in $m^2$ and k is the volumetric flow velocity measured through the membrane in $m^3 s^{-1}$ per unit area per unit pressure drop across the membrane following the membrane's exposure to gas in the reservoir, the at least two regions comprising a liquid-containing region configured to contain a liquid to be dispensed and a non-liquid-containing region configured only to contain gas;
   a perforate membrane connecting the liquid-containing region to the atmosphere, such that vibration of the membrane causes a liquid contained therein to be ejected through the perforate membrane into the atmosphere; and
   a pressure control system comprising one or more valves, wherein all of the valves that are a part of the pressure control system are only connected to the non-liquid-containing region of the reservoir, in which:
      at least one valve is configured only to allow gas to leave the non-liquid containing region of the reservoir in response to a pressure difference ($\Delta P$) across the at least one valve of a certain amount, $\Delta P_{out}$, wherein 0 kPa<$\Delta P_{out}$<+0.1 kPa; and
      at least one valve is configured only to allow gas to enter the non-liquid containing region of the reservoir in response to a pressure difference ($\Delta P$) across the at least one valve of a certain amount, $\Delta P_{in}$, wherein −0.1 kPa>$\Delta P_{in}$>−10 kPa;
   wherein the pressure difference ($\Delta P$) is the absolute pressure of the gas in the non-liquid-containing region of the reservoir minus the absolute atmospheric pressure, with $\Delta P_{in} < \Delta P_{out}$.

2. The droplet generation device according to claim 1 in which the pressure control system also comprises an active component that acts to increase the volume of the reservoir or extract gas from the reservoir prior to droplet generation commencing.

3. The droplet generation device according to claim 1 in which the barrier that splits the reservoir is, at least in part, flexible.

4. The droplet generation device according to claim 1, wherein the perforate membrane and the liquid containing region of the reservoir are in a cartridge, and at least part of the pressure control system is in a master unit, wherein the cartridge is configured to be combined with the master unit to form the droplet generation device.

5. The droplet generation device according to claim 1 in which a porous media is in contact with the back side of the perforate membrane.

6. The droplet generation device according to claim 1 in which a seal is provided to disconnect the connection provided by the perforate membrane between the liquid-containing region and the atmosphere.

7. The droplet generation device according to claim 2 in which a seal is provided to disconnect, when the device is not in use, the connection provided by the perforate membrane between the liquid-containing region and the atmosphere, wherein the movement of the seal is coupled to the activation of an active component of the pressure control system.

8. The droplet generation device according to claim 1 in which the perforate membrane has been treated to make at least part of its surface hydrophobic.

9. The droplet generation device according to claim 1, wherein the pressure control system includes two valves, with a first one of the valves controlling flow in a first direction and a second one of the valves controlling flow in a second direction, opposite the first direction.

10. The droplet generation device according to claim 9, wherein the first valve controls $\Delta P_{in}$ and is sealed substantially tight when the pressure difference across the first valve is zero.

11. The droplet generation device according to claim 9, wherein the second valve controls $\Delta P_{out}$ and is non-sealed at zero pressure difference.

12. The droplet generation device according to claim 1, wherein the pressure control system also includes an active component configured to draw air out of the reservoir before ejection of the liquid into the atmosphere.

* * * * *